United States Patent [19]

Nugent

[11] 4,451,665

[45] May 29, 1984

[54] PROCESS FOR DIMERIZING ACRYLATES AND METHACRYLATES

[75] Inventor: William A. Nugent, Wilmington, Del.

[73] Assignee: E. I. Du Pont de Nemours and Company, Wilmington, Del.

[21] Appl. No.: 454,575

[22] Filed: Dec. 30, 1982

[51] Int. Cl.$^3$ ............................................. C07C 67/343
[52] U.S. Cl. .................................. 560/202; 260/429 J; 562/598; 502/167
[58] Field of Search ........................ 560/202; 562/598; 252/429 R, 431 N; 260/429 J

[56] References Cited

U.S. PATENT DOCUMENTS

| | | | |
|---|---|---|---|
| 3,013,066 | 12/1961 | Alderson | 560/202 |
| 3,074,999 | 1/1963 | Rauhut et al. | 560/202 |
| 3,322,819 | 5/1967 | Schreyer | 560/202 |
| 3,342,853 | 9/1967 | Nemec et al. | 560/202 |
| 3,342,854 | 9/1967 | Nemec et al. | 560/202 |
| 3,803,254 | 4/1974 | Hattori et al. | 560/202 X |

FOREIGN PATENT DOCUMENTS 2249389  5/1973  Fed. Rep. of Germany .
1355917 10/1972  United Kingdom .

OTHER PUBLICATIONS

Barlow et al., J. Organometal. Chem., 21, 215–226 (1970).
Oehme et al., Tetrahedron Letters, 1979, (4), 343–344.
Sen et al., J. Am. Chem. Soc., 103, 4627–4629 (1981).

Primary Examiner—Glennon H. Hollrah
Assistant Examiner—Vera C. Clarke

[57] ABSTRACT

Catalytic process for dimerizing a lower alkyl acrylate or methacrylate by contacting, at about 0° to about 150° C., the acrylate or methacrylate with the catalyst of the formula $(RCN)_4PdX_2$ wherein R is hydrocarbyl which contains no carbon-carbon unsaturation other than aromatic unsaturation and X is an anion which is incapable of displacing RCN from the cationic moiety of the palladium complex.

10 Claims, No Drawings

PROCESS FOR DIMERIZING ACRYLATES AND METHACRYLATES

DESCRIPTION

1. Technical Field

This invention relates to an improved process for dimerizing esters of acrylic acid and methacrylic acid to esters of, respectively, hexenedioic acid and dimethylhexenedioic acid.

2. Background

Certain palladium compounds are known to catalyze the dimerization of alkyl acrylates. For example, in the presence of bis(benzonitrile)palladium(II) chloride, $(C_6H_5CN)_2PdCl_2$, methyl acrylate is dimerized in 67% conversion and 93% yield to 90% linear dimers in 23 hours at 113° C., as disclosed by Barlow et al., J. Organometal. Chem., 21, 215 (1970). The rate of reaction can be increased by adding silver tetrafluoroborate, $AgBF_4$, to the reaction mixture, for example, as disclosed by Oehme et al., Tetrahedron Letters, 1979(4), 343.

In contrast to the dimerization reaction, other palladium complexes are known as catalysts for polymerization reactions. For example, Sen et al., J. Am. Chem Soc., 103, 4627 (1981), disclose the use of $(CH_3CN)_4Pd(BF_4)_2$ as a catalyst for the polymerization of styrene. Use of the catalyst with ethylene provided butenes, hexenes and octenes. Sen et al., Organometallics, 1, 415 (1982) disclose that no polymerization was observed when this catalyst was used with acrylonitrile and methyl acrylate. U.S. Pat. No. 3,803,254 discloses a wide variety of palladium complexes as catalysts for the production of oligomers and chain oligomers from vinyl aromatic compounds, optionally in the presence of an α-monoolefin. Included among the many catalysts disclosed are palladium complexes containing acetonitrile or benzonitrile and tetrafluoroborate as the anion.

U.S. Pat. No. 3,322,819 discloses the hydrodimerization of alkyl methacrylate to dialkyl 2,2,4-trimethylpentanedioate (called 2,2,4-trimethylglutarate) in the presence of a cobalt or ruthenium carbonyl derivative.

Dialkyl hexenedioates are readily convertible to adipic acid (hexanedioic acid) by hydrogenation and subsequent hydrolysis. Adipic acid in turn is used in large volume in the production of condensation polymers, particularly 66 nylon. Therefore, even a small improvement in a method for making dialkyl hexenedioates can be of major commercial significance.

A system that will catalyze the dimerization of methacrylate esters to "linear" diesters, that is, 2,5-dimethylhexenedioates, which are the products having the longest possible chain with terminal alkoxycarbonyl groups, is also a desirable objective. 2,5-Dimethylhexanedioic acid, available from dialkyl 2,5-dimethylhexenedioates, is also useful in making condensation polymers such as polyamides and polyesters.

It is an object of this invention to provide an improved process for producing dialkyl hexenedioates and dialkyl 2,5-dimethylhexenedioates by the catalytic dimerization of, respectively, alkyl acrylates and alkyl methacrylates. It is a further object to provide such a process which employs both known and heretofore unknown palladium complexes as the catalyst, either of which can be made by known processes or modified known processes. Another object is to provide a dimerization process which is silver free and provides high selectivity to linear, that is, unbranched, dimers at lower dimerization temperatures and with higher conversions and yields than prior art processes. Other objects will become apparent hereinafter.

DISCLOSURE OF INVENTION

For further comprehension of the invention and of the objects and advantages thereof, reference may be made to the following description and the appended claims in which the various novel features of the invention are more particularly set forth.

It has been discovered that a family of nitrile-palladium complexes, some of which are novel compounds, catalyzes the dimerization of acrylate esters in good conversions and yields to give products containing very high percentages of linear dimers. The same catalysts bring about conversion of methacrylate esters to 100% linear dimers in good conversion and yields, which is contrary to what may be expected in the absence of known published references to linear methacrylate dimerization.

The invention resides in the process which comprises contacting a lower alkyl acrylate or a lower alkyl methacrylate, with lower alkyl being alkyl of 1 to 8 carbon atoms, with the palladium(II) complex of the formula $(RCN)_4PdX_2$, optionally, but preferably, in the presence of a lithium promoter LiZ, and optionally in the presence of an oxidant for metallic palladium, preferably in the presence of both the promoter and the oxidant, with R, X and Z being defined below, at a temperature of about 0° C. to about 150° C., more preferably to about 100° C., still more preferably, about 20° C. to about 70° C., to produce one or more dialkyl hexenedioates (from the alkyl acrylate) or a dialkyl 2,5-dimethylhexenedioate (from the alkyl methacrylate). In the aforesaid formula R is hydrocarbyl that is free of ethylenic or acetylenic unsaturation; in other words, any unsaturation in R is aromatic. Stated somewhat differently, R is hydrocarbyl which contains no carbon-carbon unsaturation other than aromatic unsaturation. Because of more ready availability of the nitriles, R generally is alkyl, cycloalkyl or mixed alkyl-cycloalkyl of 1 to 18 carbon atoms, or aryl, aralkyl, alkaryl or alkaralkyl of 6 to 12 carbon atoms, for example, methyl, ethyl, isopropyl, t-butyl, neopentyl, hexyl, 2-ethylhexyl, decyl, dodecyl, tetradecyl, octadecyl, cyclopentyl, methylcyclopentyl, cyclohexyl, cyclohexylethyl, cycloheptyl, phenyl, naphthyl, biphenylyl, benzyl, phenethyl, tolyl, xylyl, butylphenyl, naphthylmethyl, methylbenzyl and cumyl. Preferably, because of more ready availability, R is lower alkyl of 1 to 8 carbon atoms or phenyl.

Each of X and Z in the aforesaid formulas is an anion which is incapable of displacing RCN from the cationic moiety of the palladium compound. More specifically, each of X and Z must be such that $(RCN)_4Pd^{++} + 2X^-$ or $2Z^- \leftrightarrow (RCN)_2PdX_2$(or $Z_2$) $+ 2RCN$. Examples of operable X and Z include $BF_4^-$, $PF_6^-$, $ClO_4^-$, $SbF_6^-$ and $AsF_6^-$. Inoperable would be $Cl^-$. Although, in any given system, X and Z can be the same or different, it may be preferable, for purpose of regeneration of the palladium catalyst and the lithium promoter, that X and Z be the same. In the process preferred herein, X is $PF_6^-$ and Z is $BF_4^-$ since this combination gives superior results.

When a lithium promoter is used, the atomic Li/Pd ratio usually is about 0.5/1 to 100/1, preferably about 20/1 to 40/1.

The size of the alkyl group in the alkyl acrylate or alkyl methacrylate is not critical. However, lower alkyl, of 1 to 8 carbon atoms, acrylates and methacrylates are preferred because of their availability, and the methyl and ethyl esters are especially preferred because of the ease of isolation of the resultant reaction products. The alkyl group can be substituted with any group that does not interfere with the desired reaction.

The amount of palladium catalyst charged depends largely on the amount of alkyl acrylate or methacrylate used, and the ratio of moles of alkyl acrylate or alkyl methacrylate to gram atoms of palladium can vary widely. Usually, to permit efficient use of the catalyst, the ratio is at least 10/1 and can be as high as about 10,000/1. Preferably, the ratio is about 100/1 to 800/1, more preferably about 150/1 to 200/1.

Although the dimerization reaction itself does not involve the reduction of the palladium(II) in the catalyst, in practice, the palladium is gradually reduced to inactive palladium(0) through side reactions. This is not surprising in view of the known tendency of palladium to undergo this change. To maintain the palladium in its starting oxidation state of +2, and thereby increase catalyst efficiency, an oxidant preferably is incorporated into the reaction mixture. The oxidant can be organic (for example, benzoquinone, as in Example 8) or inorganic (for example, vanadium oxytrifluoride, as in Example 3) and, since it must be capable of oxidizing Pd(0) to Pd(II), it should not coordinate so strongly with palladium that it interferes with the mechanism of catalysis. Over a relatively broad range, the ratio of equivalents of oxidant to gram atoms of palladium is not critical. Usually, the ratio is about 1/1 to 20/1, preferably about 2/1 to 10/1.

The process can be conducted over a rather broad temperature range, for example, about 0° C. to about 150° C., although 100° C. is a preferred maximum. The temperature chosen will depend on such variables as the particular acrylate or methacrylate to be dimerized, the catalyst concentration, the promoter/catalyst ratio when a promoter is used, and the time over which it is convenient or desired to operate the process. More preferably, the reaction temperature is about 20° C. to about 70° C. The time can vary widely, from a few minutes to several days. Preferably, the reaction is carried out in about 15 minutes to 72 hours.

The process of the invention has these advantages over prior art processes using, for example, a catalyst such as $(C_6H_5CN)_2PdCl_2$: it is operable at lower temperatures; it gives higher conversions of starting materials and yields of dimers; and it gives much higher ratios of linear dimer to branched dimer in the product, that is, it is highly selective in the formation of linear dimers. Although it is known in the art that the addition of $AgBF_4$ to $(C_6H_5CN)_2PdCl_2$ increases the rate of the dimerization reaction, such addition provides the following disadvantages: the cost of the silver adds to the expense of the palladium; reactivation of the catalyst becomes more complicated; and the ultimate catalyst turnover is less than with the catalyst used in the process of the invention. Catalyst turnover, which is a measure of catalyst efficiency and which, in this disclosure, is limited to palladium turnover, is defined as moles of dimer product divided by gram atoms of palladium. Palladium turnover is discussed further below.

The following examples are intended as illustrative of the invention. All temperatures are in degrees Celsius. The nitriles used in the catalyst preparations and the acrylates and methacrylates to be dimerized were dried over 4 A molecular sieves prior to use. The syntheses of the palladium catalysts are described in the examples; all other materials employed were reagent-grade chemicals, used as received from the vendors. The syntheses of the palladium catalysts and the room-temperature dimerization experiments were carried out in a Vacuum/Atmospheres Company drybox. Dimerization experiments at higher temperatures were carried out under nitrogen in a thermostatically controlled oil bath in a stirred round-bottom flask equipped with a reflux condenser. Gas-chromatographic analyses were carried out on a 12'×⅛" (3.66 m × 3.2 mm) column of 10% SE-30 on 80/90 Anakrom ® ABS kieselguhr silica with injector and detector at 250°. Analyses were isothermal, with a column temperature of 180° for methyl acrylate and 200° for methyl methacrylate. The identities of the palladium complexes not reported in the literature were confirmed by elemental analyses and, for $(C_6H_5CN)_4Pd(BF_4)_2$ and $(C_6H_5CN)_4Pd(PF_6)_2$, by elemental analyses and by infrared spectroscopic analyses. The $(RCN)_4PdX_2$ complexes can be prepared by treatment of NOX salts with Pd in the presence of the appropriate RCN, in substantial accordance with the procedure of Schramm and Wayland, Chemical Communications, 1968, 898.

Conversion of the starting acrylate or methacrylate, expressed as a percent, is defined as 100 times the moles of ester consumed divided by the moles of ester charged, that is, 100 times [(moles of ester charged)−(moles of ester recovered)] divided by the moles of ester charged. "Yield" is used in the general sense, as an indication or measure of the amount of dimer product produced. For comparative purposes, yield is reported in terms of palladium turnover, defined above and expressed as mol (of dimer product)/(g. atom) Pd. For a given yield to be considered as a fraction or percent of the highest value that can be realized in a particular system, the maximum possible turnover must be considered. Maximum turnover is defined as one-half the moles of acrylate or methacrylate charged divided by gram atoms of palladium in the catalyst, and is also expressed as (mols of acrylate or methacrylate)/2(g. atom of Pd).

EXAMPLE 1

This example demonstrates catalysis by an $(RCN)_4PdX_2$ complex and provides a comparison with a prior art $(C_6H_5CN)_2PdCl_2/AgBF_4$ catalyst such as disclosed by Oehme et al., loc. cit.

A. Tetrakis(acetonitrile)palladium(II) tetrafluoroborate, $(CH_3CN)_4Pd(BF_4)_2$, was prepared by the method of Schramm and Wayland, Chemical Communications, 1968, 898. A mixture of methyl acrylate (50 mL), $(CH_3CN)_4Pd(BF_4)_2$ (0.44 g, 1.0 mmol), and decane (1.0 mL; internal standard) was stirred at 60°. GC (gas chromatography) analysis after 0.5 h indicated the formation of dimethyl dihydromuconates (dimers) as a mixture of isomers (3 mol/Pd). After 1 h the amount of dimers had increased (7 mol/Pd) and after 19 h a turnover of 44 mol/Pd was obtained.

B. An identical 50-mL sample of methyl acrylate was contacted with bis(benzonitrile)palladium dichloride (0.38 g, 1.0 mmol), silver tetrafluoroborate (0.39 g; 2.0 mmol), and decane (1.0 mL). The mixture was stirred at 60° for 0.5 h, whereupon GC analysis indicated dimer formation (25 mol/Pd). Continued heating for 18 h caused no further increase in the yield of dimer. These results show that although the dimerization reaction in the presence of the prior art catalyst started out relatively fast, no further reaction was noted after about 0.5 h due to the loss of the activity of the catalyst. On the other hand, the catalyst of Part A was active much longer and ultimately gave higher turnovers to dimers.

EXAMPLE 2

This example demonstrates catalysis by an $(RCN)_4PdX_2$ complex in conjunction with a lithium promoter.

The dimerization reaction was carried out by substantially the same method described in Example 1A, except that the catalyst included the promoter lithium tetrafluoroborate, $LiBF_4$, (3.0 g, 32 mmol). GC analysis showed that dimers were formed at an increased rate, compared with Example 1A (32 mol/Pd in 0.5 h; 40 mol/Pd in 4.5 h).

EXAMPLE 3

This example demonstrates catalysis by an $(RCN)_4PdX_2$ complex in conjunction with $VOF_3$ as an oxidant for the palladium in the catalyst; the oxidant extends the life of the catalyst.

The dimerization reaction was carried out by substantially the same method described in Example 1A, except that the catalyst included the oxidant vanadium(V) oxytrifluoride, $VOF_3$, (1.0 g, 8.0 mmol) as an oxidant for the reduced palladium. GC analysis showed yields of dimer of 30 mol/Pd after 0.5 h, 45 mol/Pd after 1 h, and 68 mol/Pd after 72 h.

EXAMPLE 4

This example demonstrates catalysis by an $(RCN)_4PdX_2$ complex and provides a comparison with the prior art catalyst of Example 1B.

A. Tetrakis(benzonitrile)palladium(II) hexafluorophosphate, $(C_6H_5CN)_4Pd(PF_6)_2$, was prepared, using a modification of the method used in Example 1A, by reacting palladium sponge in 10:1 methylene chloride:- benzonitrile and nitrosonium hexafluorophosphate at 25°. The insoluble product was collected by filtration and volatile impurities were removed in a vacuum chamber at 25°.

A mixture of methyl acrylate (50 mL) and tetrakis(- benzonitrile)palladium(II) hexafluorophosphate (0.81 g, 1.0 mmol) was stirred overnight (about 18 h) at 25°. Undecane (1.0 mL) was added as an internal standard, and the yield of dimer was determined by GC (55 mol/Pd).

B. An identical 50-mL sample of methyl acrylate was contacted with bis(benzonitrile)palladium dichloride (0.38 g, 1.0 mmol) and silver tetrafluoroborate (0.39 g, 2.0 mmol). The mixture was stirred at 25° until precipitation of metallic palladium was complete, corresponding to complete deactivation of the catalyst (3 h). GC analysis showed substantially less dimer formation (24 mol/Pd) than in Part A.

EXAMPLE 5

This example demonstrates the very high catalyst turnovers and long catalyst life that can be realized by means of an $(RCN)_4PdX_2$ complex in conjunction with a lithium promoter.

Using a modification of the method used in Example 1A, tetrakis(acetonitrile)palladium(II) hexafluorophosphate, $(CH_3CN)_4Pd(PF_6)_2$, was prepared by reacting palladium sponge as a suspension in acetonitrile and nitrosonium hexafluorophosphate. The resultant solution was filtered and, after precipitation was effected by adding diethyl ether, the desired product was collected by filtration; volatile impurities were removed in a vacuum chamber at 25°.

A mixture of methyl acrylate (50 mL), tetrakis- (acetonitrile) palladium(II) hexafluorophosphate (0.55 g, 1.0 mmol), and the promoter lithium tetrafluoroborate(3.0 g, 32 mmol) was stirred for 10 days at 25°. GC analysis showed a high yield of dimer (160 mol/Pd). The reaction mixture was then heated 24 h at 35°, whereupon the dimer yield increased (200 mol/Pd). The mixture was heated an additional 24 h at 60°, resulting in another increase in dimer yield (220 mol/Pd). The maximum turnover realizable in this system, corresponding to a 100% conversion of methyl acrylate to dimer, is 280.

EXAMPLE 6

This example represents an especially preferred embodiment of the invention with methyl acrylate.

A. A mixture of methyl acrylate (50 mL), tetrakis- (acetonitrile)palladium(II) hexafluorophosphate (1.68 g, 3.0 mmol), lithium tetrafluoroborate (9.0 g, 96 mmol), and undecane (1.0 mL) was stirred at 40° for 17 h. GC analysis of the product mixture showed that 90% of the starting methyl acrylate had been converted to dimers (82 mol/Pd; maximum turnover 92 mol/ Pd); the only other components observed by GC were the undecane internal standard and a small amount of methyl propionate that was present in the starting methyl acrylate as an impurity.

Petroleum ether (300 mL) was added to the reaction mixture; two liquid layers were formed. The upper layer was removed and the solvent was distilled off to provide substantially pure dimer (believed to be greater than 99% pure), shown by elemental analysis and NMR spectroscopic analysis to consist of a 7:1 mixture of the 2 and 3 isomers of dimethyl dihydromuconate (dimethyl 2-hexenedioate and dimethyl 3-hexenedioate). The lower layer (a yellow oil) containing recovered catalyst and additional dimers was added to fresh methyl acrylate and was shown to be active for acrylate dimerization.

B. Part A was repeated except that ⅓ the amounts were used, that is, 0.56 g of $(CH_3CN)_4Pd(PF_6)_2$ and 3.0 g of $LiBF_4$, and the dimerization was carried out at ambient temperature for about 66 h; the recovered product was hydrogenated over palladium on charcoal. GC analysis showed that 99.5% of the resultant dihydrodimer product so produced was dimethyl adipate (linear), with only 0.5% of the branched dimethyl methylglutarate being formed.

EXAMPLE 7

This example demonstrates the use of pivalonitrile, $(CH_3)_3CCN$, as a ligand in the $(RCN)_4PdX_2$ complex.

Tetrakis(pivalonitrile)palladium(II) hexafluorophosphate, $[(CH_3)_3CCN]_4Pd(PF_6)_2$, was prepared using a modification of the method used in Example 1A, by treating a suspension of palladium sponge in pivalonitrile with nitrosonium hexafluorophosphate at 25°. The insoluble product was collected by filtration and volatile impurities were removed in a vacuum chamber at 25°.

A mixture of methyl acrylate (50 mL), tetrakis(- pivalonitrile)palladium(II) hexafluorophosphate (0.61 g, 1.0 mmol), lithium tetrafluoroborate (3.0 g, 32 mmol), and undecane (1.0 mL) was stirred for 18 h at 25°. GC analysis indicated formation of dimers (24 mol/Pd).

EXAMPLE 8

This example demonstrates catalysis by an $(RCN)_4PdX_2$ complex in conjunction with benzoquinone as an oxidant for the palladium in the catalyst.

A. A mixture of methyl acrylate (50 mL), tetrakis(benzonitrile)palladium(II) tetrafluoroborate (0.69 g, 1.0 mmol) and benzoquinone (1.0 g, 10 mmol) was stirred at 25° for 3 h. GC analysis showed a high yield of dimers (147 mol/ Pd).

B. In a control experiment the reaction was carried out as in Part A but without the benzoquinone. After 18 h of reaction time, GC analysis showed a lower amount of dimer formation (32 mol/Pd).

EXAMPLE 9

A mixture of methyl methacrylate (50 mL), lithium tetrafluoroborate (3.0 g, 32 mmol), tetrakis(benzonitrile)palladium(II) tetrafluoroborate (0.56 g, 1.0 mmol) and undecane (1.0 mL) was stirred for 23 h at 25°. GC analysis showed formation (14 mol/Pd) of a mixture of isomeric linear dimers, dimethyl 2,5-dimethylhexenedioates.

EXAMPLE 10

A mixture of ethyl acrylate (25 mL), trifluoroethyl acrylate (25 mL), and tetrakis(benzonitrile)palladium(II) tetrafluoroborate (0.69 g, 1.0 mmol) was stirred at 60° for 8 h. GC analysis showed the presence of diethyl dihydromuconate, suggesting that codimerization of the trifluoroethyl acrylate did not take place.

EXAMPLE 11

A mixture of ethyl acrylate (50 mL), tetrakis(acetonitrile)palladium(II) tetrafluoroborate (1.33 g, 3.0 mmol), and lithium tetrafluoroborate (9.0 g, 96 mmol) was stirred at 40° for 30 h. The product was added to 100 mL of water; the resultant mixture was extracted twice with 100 mL of ether. The solvent was distilled off and the residue was distilled at 83°-85° and 0.1 torr. The product (34 g, 57 mol/Pd, 74% conversion of starting monomer) was shown by GC to consist of the linear dimer diethyl dihydromuconate (93% 2 and 7% 3).

EXAMPLE 12

This example demonstrates the use of lithium hexafluorophosphate as a promoter.

A mixture of methyl methacrylate (50 mL), tetrakis(acetonitrile)palladium(II) hexafluorophosphate (1.68 g, 3.0 mmol), and lithium hexafluorophosphate (14.3 g, 96 mmol) was heated at 40° with stirring for about 18 h. It appeared that not all of the solids had dissolved (stirring may have been lost temporarily). GC analysis indicated that dimethyl 2,5-dimethylhexenedioates had been formed in about 20% conversion.

EXAMPLE 13

This example represents an especially preferred embodiment of the invention with methyl methacrylate.

A mixture of methyl methacrylate (50 mL), tetrakis(acetonitrile)palladium(II) hexafluorophosphate (1.68 g, 3.0 mmol), and lithium tetrafluoroborate (9.0 g, 96 mmol) was stirred at 25°. After 72 h diethyl ether (100 mL) was added and the resultant mixture was extracted first with aqueous saturated sodium bicarbonate and then with aqueous saturated sodium chloride. The organic layer was filtered and the solvent and unreacted methyl methacrylate were distilled off under nitrogen. Distillation of the residue in high vacuum (about 0.1 torr) at 43°-53° (mostly 52°-53°) afforded 29.6 g (63%) of a colorless liquid product which was shown by GC analysis, elemental analysis, and NMR spectroscopic analysis to be a mixture of isomeric dimethyl 2,5-dimethylhexenedioates consisting of 94% of the 2 isomer and 6% of the 3 isomer. Anal. Calcd for $C_{10}H_{16}O$: C, 59.98; H, 8.07; Found: C, 60.33, 59.48; H, 8.24, 8.08.

BEST MODE FOR CARRYING OUT THE INVENTION

It is my present belief that the best mode for carrying out the invention is represented by the examples herein.

INDUSTRIAL APPLICABILITY

The industrial applicability of dimerization products of acrylates and methacrylates is well known. For example, after removal of residual olefinic unsaturation, the resultant diesters can be used in the formation of polyesters; the corresponding diacids can be used in the formation of polyamides.

Although preferred embodiments of the invention have been described and illustrated above, it is to be understood that there is no intent to limit the invention to the precise constructions herein disclosed and it is to be further understood that the right is reserved to all changes and modifications coming within the scope of the invention as defined in the appended claims.

I claim:

1. Catalytic dimerization process comprising contacting, at about 0° to about 150° C., a lower alkyl acrylate or lower alkyl methacrylate, with lower alkyl being alkyl of 1 to 8 carbon atoms, with the catalyst which is the palladium complex of the formula $(RCN)_4PdX_2$ wherein R is hydrocarbyl which contains no carbon-carbon unsaturation other than aromatic unsaturation and X is an anion which is incapable of displacing RCN from the cationic moiety of the palladium complex, to produce dimer of the lower alkyl acrylate or methacrylate.

2. Process of claim 1 where R is alkyl, cycloalkyl or mixed alkyl-cycloalkyl of 1 to 18 carbon atoms or aryl, aralkyl, alkaryl or alkaralkyl of 6 to 12 carbon atoms.

3. Process of claim 2 wherein the temperature is about 20° C. to about 70° C.

4. Process of claim 1 wherein X is $BF_4^-$, $PF_6^-$, $ClO_4^-$, $SbF_6^-$ or $AsF_6^-$.

5. Process of claim 1 wherein there is also present a lithium promoter of the formula LiZ wherein Z is an anion which is incapable of displacing RCN from the cationic moiety of the palladium complex.

6. Process of claim 5 wherein X is $PF_6^-$, Z is $BF_4^-$, R is methyl and the lower alkyl acrylate or methacrylate is methyl acrylate or methacrylate.

7. Process of claim 5 wherein the atomic Li/Pd ratio is about 0.5/1 to 100/1.

8. Process of claim 7 wherein the ratio is 20/1 to 40/1.

9. Process of claim 1 wherein the ratio of the moles of alkyl acrylate or methacrylate to gram atoms of palladium is 10/1 to 10,000/1.

10. Process of claim 1 wherein there is also present an oxidant for zero valent palladium which is formed in side reactions.

* * * * *